United States Patent
Petersen (10) Patent No.: US 7,708,761 B2
(45) Date of Patent: May 4, 2010

(54) SPINAL PLUG FOR A MINIMALLY INVASIVE FACET JOINT FUSION SYSTEM

(75) Inventor: David A. Petersen, Clearwater, FL (US)

(73) Assignee: minSURG International, Inc., Clearwater, FL (US)

( * ) Notice: Subject to any disclaimer, the term of this patent is extended or adjusted under 35 U.S.C. 154(b) by 896 days.

(21) Appl. No.: 11/232,519

(22) Filed: Sep. 22, 2005

(65) Prior Publication Data

US 2006/0111782 A1 May 25, 2006

Related U.S. Application Data

(63) Continuation-in-part of application No. 10/992,720, filed on Nov. 22, 2004, now abandoned.

(51) Int. Cl.
*A61B 17/70* (2006.01)
(52) U.S. Cl. ..................................... 606/247
(58) Field of Classification Search ............. 623/16.11, 623/18.11, 17.11–17.16; 606/246–249, 60, 606/95–99
See application file for complete search history.

(56) References Cited

U.S. PATENT DOCUMENTS

| | | |
|---|---|---|
| 4,344,190 A | 8/1982 | Lee et al. |
| 4,501,269 A * | 2/1985 | Bagby .................. 606/279 |
| 4,654,314 A | 3/1987 | Takagi et al. |
| 4,737,411 A | 4/1988 | Graves, Jr. et al. |
| 4,834,757 A | 5/1989 | Brantigan |
| 4,878,915 A | 11/1989 | Brantigan |
| 4,961,740 A | 10/1990 | Ray et al. |
| 4,990,161 A | 2/1991 | Kampner |
| 5,009,666 A | 4/1991 | Van Syckle et al. |

(Continued)

FOREIGN PATENT DOCUMENTS

WO 0062684 10/2000

(Continued)

OTHER PUBLICATIONS

Stein, M. et al, Percutaneous Facet Joint Fusion: Preliminary Experience, J.Vasc. Interv. Radiol., 1993, Jan.-Feb., 4(1) 69-74.

(Continued)

*Primary Examiner*—Alvin J. Stewart
(74) *Attorney, Agent, or Firm*—Sheppard, Mullin, Richter & Hampton LLP; Don J. Pelto (57) ABSTRACT

A frustum shaped body has an aperture in a top surface and a pair of first and second opposed apertures in a side surface, first and second horizontal internal channels connect both the first and second opposed apertures. A vertical channel from the top aperture connects with the first and second channels. After the body is inserted into a hole in a facet joint, compatible synthetic or biologic material is inserted into the vertical channel until the material exits from the first and second apertures in the side surface. At least one pair of flanges on a portion of an exterior side surface of the body acts as a detent to hold the body in place within the facet joint hole.

20 Claims, 11 Drawing Sheets

U.S. PATENT DOCUMENTS

| | | | |
|---|---|---|---|
| 5,015,247 A | 5/1991 | Michelson | |
| 5,026,373 A | 6/1991 | Ray et al. | |
| 5,152,791 A | 10/1992 | Hakamatsuka et al. | |
| 5,298,254 A | 3/1994 | Prewett et al. | |
| 5,425,772 A | 6/1995 | Brantigan | |
| 5,445,639 A * | 8/1995 | Kuslich et al. | 606/80 |
| 5,527,312 A | 6/1996 | Ray | 606/301 |
| D374,283 S * | 10/1996 | Michelson | D24/135 |
| 5,593,409 A | 1/1997 | Mechelson | |
| 5,645,598 A | 7/1997 | Brosnahan, III | |
| 5,683,391 A | 11/1997 | Boyd | |
| 5,709,683 A | 1/1998 | Bagby | |
| 5,769,897 A | 6/1998 | Harle | |
| 5,782,919 A | 7/1998 | Zdeblick et al. | |
| 5,785,710 A | 7/1998 | Michelson | |
| D397,436 S * | 8/1998 | Michelson | D24/135 |
| 5,814,084 A | 9/1998 | Grivas et al. | |
| 5,860,973 A | 1/1999 | Michelson | |
| 5,865,847 A * | 2/1999 | Kohrs et al. | 128/898 |
| 5,897,556 A | 4/1999 | Drewry et al. | |
| 5,899,939 A | 5/1999 | Boyce et al. | |
| 5,906,616 A | 5/1999 | Pavlov et al. | |
| 5,928,242 A * | 7/1999 | Kuslich et al. | 606/96 |
| D412,435 S * | 8/1999 | Cultice, Jr. | D8/397 |
| 5,968,098 A * | 10/1999 | Winslow | 623/17.11 |
| 5,984,922 A | 11/1999 | McKay | |
| 6,004,326 A * | 12/1999 | Castro et al. | 606/99 |
| 6,033,419 A * | 3/2000 | Hamblin et al. | 606/184 |
| 6,033,438 A | 3/2000 | Bianchi et al. | |
| 6,039,762 A * | 3/2000 | McKay | 623/17.11 |
| 6,042,582 A * | 3/2000 | Ray | 606/86 A |
| 6,045,580 A * | 4/2000 | Scarborough et al. | 623/17.11 |
| 6,048,580 A | 4/2000 | Scarborough et al. | |
| 6,053,916 A | 4/2000 | Moore | |
| D424,421 S * | 5/2000 | Ono | D8/397 |
| 6,063,088 A * | 5/2000 | Winslow | 606/86 A |
| RE36,758 E * | 6/2000 | Fitz | 623/17.11 |
| 6,080,155 A * | 6/2000 | Michelson | 606/86 A |
| 6,083,225 A * | 7/2000 | Winslow et al. | 606/86 A |
| 6,096,081 A | 8/2000 | Grivas et al. | |
| 6,111,164 A | 8/2000 | Rainey et al. | |
| 6,117,174 A | 9/2000 | Nolan | |
| 6,118,043 A | 9/2000 | Nies et al. | |
| 6,123,731 A | 9/2000 | Boyce et al. | |
| 6,143,030 A | 11/2000 | Paul et al. | |
| 6,143,033 A | 11/2000 | Paul et al. | |
| 6,149,651 A | 11/2000 | Drewry et al. | |
| 6,200,322 B1 * | 3/2001 | Branch et al. | 606/96 |
| 6,210,412 B1 * | 4/2001 | Michelson | 606/86 A |
| 6,224,630 B1 | 5/2001 | Bao et al. | |
| 6,228,111 B1 * | 5/2001 | Tormala et al. | 623/1.38 |
| 6,241,770 B1 | 6/2001 | Michelson | |
| 6,241,771 B1 | 6/2001 | Gresser et al. | |
| 6,258,125 B1 | 7/2001 | Paul et al. | |
| 6,261,586 B1 | 7/2001 | McKay | |
| 6,264,656 B1 | 7/2001 | Michelson | |
| 6,264,677 B1 * | 7/2001 | Simon et al. | 606/232 |
| 6,267,763 B1 * | 7/2001 | Castro | 606/86 A |
| 6,270,528 B1 | 8/2001 | McKay | |
| 6,302,913 B1 | 10/2001 | Ripamonti et al. | |
| 6,315,795 B1 * | 11/2001 | Scarborough et al. | 623/17.11 |
| 6,346,123 B1 * | 2/2002 | McKay | 623/17.11 |
| 6,371,986 B1 * | 4/2002 | Bagby | 623/17.11 |
| 6,371,988 B1 | 4/2002 | Pafford et al. | |
| 6,371,989 B1 | 4/2002 | Chauvin et al. | |
| 6,375,655 B1 | 4/2002 | Zdeblick et al. | |
| 6,395,035 B2 | 5/2002 | Bresina et al. | |
| 6,398,811 B1 | 6/2002 | McKay | |
| 6,409,765 B1 | 6/2002 | Bianchi et al. | |
| 6,432,436 B1 | 8/2002 | Gertzman et al. | |
| 6,436,098 B1 * | 8/2002 | Michelson | 606/86 A |
| 6,440,444 B2 | 8/2002 | Boyce et al. | |
| 6,443,987 B1 | 9/2002 | Bryan | |
| 6,452,586 B1 * | 9/2002 | Holmdahl et al. | 345/163 |
| 6,485,518 B1 * | 11/2002 | Cornwall et al. | 623/17.11 |
| 6,491,724 B1 | 12/2002 | Ferree | |
| 6,494,883 B1 | 12/2002 | Ferree | |
| 6,500,205 B1 | 12/2002 | Michelson | |
| 6,500,206 B1 * | 12/2002 | Bryan | 623/17.16 |
| 6,511,509 B1 * | 1/2003 | Ford et al. | 623/23.5 |
| 6,520,907 B1 * | 2/2003 | Foley et al. | 600/114 |
| 6,537,320 B1 | 3/2003 | Michelson | |
| 6,544,289 B2 | 4/2003 | Wolfinbarger, Jr. et al. | |
| 6,548,569 B1 | 4/2003 | Williams et al. | |
| 6,551,995 B1 | 4/2003 | Oppermann et al. | |
| 6,565,574 B2 * | 5/2003 | Michelson | 606/90 |
| 6,582,431 B1 * | 6/2003 | Ray | 606/86 A |
| 6,585,770 B1 | 7/2003 | White et al. | |
| 6,585,772 B2 * | 7/2003 | Hunter et al. | 623/23.54 |
| 6,613,091 B1 | 9/2003 | Zdeblick et al. | |
| 6,626,945 B2 | 9/2003 | Simon et al. | |
| 6,632,246 B1 | 10/2003 | Simon et al. | |
| 6,638,309 B2 | 10/2003 | Bonutti | |
| 6,641,613 B2 | 11/2003 | Sennett | |
| 6,645,206 B1 | 11/2003 | Zdeblick et al. | |
| 6,652,584 B2 | 11/2003 | Michelson | |
| 6,652,592 B1 | 11/2003 | Grooms et al. | |
| 6,669,729 B2 * | 12/2003 | Chin | 623/17.11 |
| D484,785 S * | 1/2004 | Plumer | D8/397 |
| 6,689,167 B2 * | 2/2004 | Bagby | 623/17.11 |
| 6,695,851 B2 * | 2/2004 | Zdeblick et al. | 606/96 |
| 6,695,882 B2 | 2/2004 | Bianchi et al. | |
| 6,696,073 B2 * | 2/2004 | Boyce et al. | 424/422 |
| 6,702,856 B2 | 3/2004 | Bonutti | |
| 6,709,458 B2 | 3/2004 | Michelson | |
| 6,719,795 B1 * | 4/2004 | Cornwall et al. | 623/17.11 |
| 6,743,255 B2 * | 6/2004 | Ferree | 623/17.11 |
| 6,747,121 B2 | 6/2004 | Gogolewski | |
| 6,758,849 B1 | 7/2004 | Michelson | |
| 6,790,233 B2 | 9/2004 | Brodke et al. | |
| 6,793,679 B2 | 9/2004 | Michelson | |
| 6,814,756 B1 | 11/2004 | Michelson | |
| 6,827,740 B1 | 12/2004 | Michelson | |
| 6,838,493 B2 | 1/2005 | Williams et al. | |
| 6,840,961 B2 | 1/2005 | Tofighi et al. | |
| 6,843,807 B1 * | 1/2005 | Boyce et al. | 623/23.51 |
| 6,852,125 B2 | 2/2005 | Simon et al. | |
| 6,867,247 B2 | 3/2005 | Williams et al. | |
| 6,893,462 B2 | 5/2005 | Buskirk et al. | |
| 6,902,578 B1 * | 6/2005 | Anderson et al. | 623/16.11 |
| 6,905,517 B2 | 6/2005 | Bonutti | |
| 6,923,810 B1 | 8/2005 | Michelson | |
| 6,929,647 B2 * | 8/2005 | Cohen | 606/99 |
| 6,972,035 B2 | 12/2005 | Michelson | |
| 6,986,788 B2 | 1/2006 | Paul et al. | |
| 6,989,029 B2 | 1/2006 | Bonutti | |
| 7,001,385 B2 * | 2/2006 | Bonutti | 606/60 |
| 7,008,453 B1 | 3/2006 | Michelson | |
| 7,012,034 B2 | 3/2006 | Heide et al. | |
| D521,858 S * | 5/2006 | Roy | D8/397 |
| 7,044,968 B1 * | 5/2006 | Yaccarino et al. | 623/16.11 |
| 7,048,762 B1 | 5/2006 | Sander et al. | |
| 7,056,342 B2 | 6/2006 | Michelson | |
| 7,060,096 B1 | 6/2006 | Schopf et al. | |
| 7,077,866 B2 * | 7/2006 | Gresser et al. | 623/17.16 |
| 7,087,082 B2 * | 8/2006 | Paul et al. | 623/17.11 |
| 7,087,540 B2 * | 8/2006 | Heide et al. | 501/1 |
| 7,105,023 B2 | 9/2006 | Eckman | |
| 7,118,598 B2 | 10/2006 | Michelson | |
| 7,223,269 B2 * | 5/2007 | Chappuis | 606/86 R |
| 7,241,313 B2 * | 7/2007 | Unwin et al. | 623/17.11 |
| 7,244,258 B2 * | 7/2007 | Burkus et al. | 606/90 |
| 7,300,440 B2 * | 11/2007 | Zdeblick et al. | 606/80 |
| D556,905 S * | 12/2007 | Barry | D24/155 |

| Patent/Pub No. | Date | Inventor | Class |
|---|---|---|---|
| 7,320,688 B2 * | 1/2008 | Foley et al. | 606/99 |
| D566,277 S * | 4/2008 | Barry | D24/155 |
| 7,396,360 B2 * | 7/2008 | Lieberman | 606/247 |
| 7,399,303 B2 * | 7/2008 | Michelson | 606/79 |
| 7,452,369 B2 * | 11/2008 | Barry | 606/279 |
| 7,491,205 B1 * | 2/2009 | Michelson | 606/90 |
| 7,517,358 B2 * | 4/2009 | Petersen | 606/247 |
| 7,569,054 B2 * | 8/2009 | Michelson | 606/60 |
| 2001/0020186 A1 | 9/2001 | Boyce et al. | |
| 2001/0034553 A1 | 10/2001 | Michelson | |
| 2001/0039458 A1 | 11/2001 | Boyer, II et al. | |
| 2001/0043940 A1 | 11/2001 | Boyce et al. | |
| 2001/0049560 A1 | 12/2001 | Paul et al. | |
| 2002/0029081 A1 | 3/2002 | Scarborough et al. | |
| 2002/0062153 A1 | 5/2002 | Paul et al. | |
| 2002/0072806 A1 | 6/2002 | Buskirk et al. | |
| 2002/0082700 A1 | 6/2002 | Bianchi et al. | |
| 2002/0111680 A1 | 8/2002 | Michelson | |
| 2002/0151895 A1 * | 10/2002 | Soboleski et al. | 606/61 |
| 2003/0009235 A1 * | 1/2003 | Manrique et al. | 623/23.63 |
| 2003/0028254 A1 * | 2/2003 | Hunter et al. | 623/20.21 |
| 2003/0032960 A1 | 2/2003 | Dudasik | |
| 2003/0050701 A1 | 3/2003 | Michelson | |
| 2003/0100949 A1 | 5/2003 | Michelson | |
| 2003/0144736 A1 | 7/2003 | Sennett | |
| 2004/0059425 A1 | 3/2004 | Schmieding | |
| 2004/0073309 A1 * | 4/2004 | Bianchi et al. | 623/17.11 |
| 2004/0127989 A1 * | 7/2004 | Dooris et al. | 623/13.17 |
| 2004/0138748 A1 * | 7/2004 | Boyer et al. | 623/16.11 |
| 2004/0148029 A1 | 7/2004 | Bianchi et al. | |
| 2004/0186571 A1 | 9/2004 | Brau et al. | |
| 2004/0215344 A1 | 10/2004 | Horchschuler et al. | |
| 2004/0230303 A1 * | 11/2004 | Gomes et al. | 623/16.11 |
| 2005/0004672 A1 * | 1/2005 | Pafford et al. | 623/17.11 |
| 2005/0015150 A1 | 1/2005 | Lee | |
| 2005/0049705 A1 * | 3/2005 | Hale et al. | 623/17.11 |
| 2005/0131538 A1 * | 6/2005 | Chervitz et al. | 623/17.11 |
| 2005/0149021 A1 * | 7/2005 | Tozzi | 606/61 |
| 2005/0149030 A1 * | 7/2005 | Serhan et al. | 606/73 |
| 2005/0159746 A1 * | 7/2005 | Grob et al. | 606/61 |
| 2005/0165483 A1 * | 7/2005 | Ray et al. | 623/17.11 |
| 2005/0177240 A1 * | 8/2005 | Blain | 623/17.15 |
| 2005/0197700 A1 * | 9/2005 | Boehm et al. | 623/17.11 |
| 2005/0216083 A1 | 9/2005 | Michelson | |
| 2005/0222687 A1 * | 10/2005 | Vunjak-Novakovic et al. | 623/23.63 |
| 2005/0261682 A1 * | 11/2005 | Ferree | 606/61 |
| 2005/0267578 A1 * | 12/2005 | Michelson | 623/17.11 |
| 2005/0288672 A1 * | 12/2005 | Ferree | 606/61 |
| 2006/0029186 A1 * | 2/2006 | De Villiers et al. | 378/163 |
| 2006/0036243 A1 * | 2/2006 | Sasso et al. | 606/61 |
| 2006/0041311 A1 * | 2/2006 | McLeer | 623/17.11 |
| 2006/0064099 A1 * | 3/2006 | Pavlov et al. | 606/72 |
| 2006/0106381 A1 | 5/2006 | Ferree et al. | |
| 2006/0111779 A1 | 5/2006 | Petersen | |
| 2006/0149254 A1 * | 7/2006 | Lauryssen et al. | 606/69 |
| 2006/0173543 A1 | 8/2006 | Brau et al. | |
| 2006/0247632 A1 * | 11/2006 | Winslow et al. | 606/61 |
| 2006/0276790 A1 * | 12/2006 | Dawson et al. | 606/61 |
| 2008/0177310 A1 * | 7/2008 | Reiley | 606/247 |
| 2008/0275505 A1 * | 11/2008 | Yuan et al. | 606/247 |
| 2008/0287996 A1 * | 11/2008 | Soboleski et al. | 606/247 |
| 2009/0024166 A1 * | 1/2009 | Carl et al. | 606/247 |
| 2009/0024219 A1 * | 1/2009 | McLeer | 623/17.16 |
| 2009/0030461 A1 * | 1/2009 | Hoy et al. | 606/247 |
| 2009/0036926 A1 * | 2/2009 | Hestad | 606/247 |
| 2009/0036927 A1 * | 2/2009 | Vestgaarden | 606/247 |
| 2009/0036986 A1 * | 2/2009 | Lancial et al. | 623/17.11 |

FOREIGN PATENT DOCUMENTS

WO 0141681 6/2001

OTHER PUBLICATIONS

Vamvanij, V., et al., Surgical Treatment of Internal Disc Disruption: An Outcome Study of Four Fusion Techniques, Journal of Spinal Disorders, vol. 11, No. 5, pp. 375-382.

Medical Academy of I.M. Sechenova of Moscow (RU); Feb. 21, 2006; RU 2 302 837.

Scientific Research Institute of Traumatology and Orthopedy of Novosibirsk (RU); 2204342.

Orthopedic Development Corp. v. Nutech Medical, Complaint, filed Feb. 7, 2008.

Orthopedic Development Corp. v. Nutech Medical, Counterclaim Defendants' Motion to Dismiss, Mar. 26, 2008.

Orthopedic Development Corp. v. Nutech Medical, Amended Answer and Counterclaim of Defendants, Apr. 14, 2008.

Orthopedic Development Corp. v. Nufix Inc., Complaint, filed Oct. 15, 2008.

Orthopedic Development Corp. v. Nutech Medical, Order of Dismissal, Nov. 4, 2008.

Orthopedic Development Corp. v. Nufix Inc., Order of Dismissal, Jan. 14, 2009.

Orthopedic Development Corp. v. Nufix Inc., Plaintiff's Motion for a Preliminary Injunction, Oct. 15, 2008.

* cited by examiner

SPINAL PLUG FOR A MINIMALLY INVASIVE FACET JOINT FUSION SYSTEM

PRIOR APPLICATIONS

This application is a continuation-in-part from application Ser. No. 10/992,720, filed Nov. 22, 2004, which is expressly incorporated herein by reference.

BACKGROUND OF THE INVENTION

1. Field of the Invention

The present invention relates generally to minimally invasive spine surgery and, more particularly, to using an arthroscopic type portal or open facet joint fusion surgical instrumentation for insertion of either pre-made, pre-shaped synthetic cortical bone or harvested and compacted iliac crest grafts, autologous or cadaveric allografts. The graft and fusion system is limited to the forty-eight facet joints located on the spine, C1-C2 through L5-S1.

2. Description of the Prior Art

In the United States alone, about 10% of the entire population will suffer from back pain sometime in the next twelve months. More people will contract back pain in the next year than any other injury or disease except the common cold and flu. About one-third will not recover and have to live with persistent, disabling symptoms. The number is cumulative year after year.

One of the root causes of back pain, particularly the persistent and disabling kind, are facet joints, small joints located behind adjacent vertebrae in the spine that allow for spinal motion.

Present surgical solutions available for the millions of people with facet joint dysfunctions are complex, invasive, pedicle screw based high-risk operations with prolonged recovery times, from 6 to 24 months, and uncertain outcomes. High risk equates to frequent litigation, which forces non-surgical symptomatic treatment while the disease or consequences of injury progressively worsen. Some of these efforts provide intervertebral fusion described in U.S. Pat. No. 6,485,518 and U.S. Patent Application Serial Number 2003/0032960. Numerous patents have been granted for general fusion of the spine that may or may not involve the facet joint by proximity or design.

With the advent of new, safer and less invasive surgical techniques and technology, the growth of spine surgery now outpaces every other orthopedic surgery segment. Its growth is further fueled by an enormous demand.

SUMMARY OF THE INVENTION

The use of pre-shaped, harvested or synthetic bone as a structural fixation for facet joint fusion offers three distinct advantages over pedicle or compression screws, which are presently used in facet fusion procedures; i.e., (1) using bone instead of metal allowing for natural bone ingrowth and a stronger, permanent fusion; and (2) the natural or synthetic graft cannot work its way loose over time, a concern with screw type fixation.

The grafts and system are specifically designed for use in a minimum invasive or an arthroscopic type portal for stand-alone procedures and provide a stronger, unique and superior fusion when used as an adjunct to instrumented vertebral fusion by greatly reducing risk of facet joint pain resulting from persistent facet joint motion.

The instrumentation, grafts and method are specifically designed for use in an arthroscopic type portal for stand-alone procedures and provides a stronger, unique and superior fusion when used as an adjunct to instrumented vertebral fusion by eliminating the risk of collateral post-operative facet joint pain resulting from additional stress placed on facet joints by the instrumentation itself.

The minimally invasive facet joint fusion for the treatment of a diseased or painful facet joint that is not appropriate for resurfacing or replacement, involves the use of instrumentation and autograft, cadaveric allograft or FDA approved pre-made, pre-shaped synthetic cortical bone graft for use in minimally invasive, outpatient, arthroscopic spine surgery or classic open surgery and, more specifically, to fuse spinal facet joints from C1-C2 through L5-S1. This system serves as a primary or a revision surgery.

The present invention accomplishes a superior spinal facet joint fusion by providing a grafting alternative to facilitate fusion using arthroscopic portal or open surgical techniques of the C1-C2 through L5-S1 spinal facet joints.

According to one broad aspect of the present invention, the arthroscopic facet joint fusion system comprises a punch or drill that creates a hole through both sides of the facet joint in a conical pattern. The hole is filled with either the patient's own harvested and compacted bone plug using iliac crest autograft, pre-made, pre-shaped cortical cadaveric allograft (the autograft or allograft formed by bone plug press or machining) or FDA approved pre-made, pre-shaped synthetic grafts.

The punch or drill includes any number of components capable of performing the creation of a hole through both sides of the spinal facet joint using an arthroscope or similar portal to access the joint or during classic open surgery. By way of example only, the punch/drill includes a hand actuator that will create sufficient pressure to create a specific sized hole through both sides of the spinal facet joint using a mechanical arrangement similar to that of common pliers resized to work through an arthroscopic opening. Additionally, a drill guide can be placed and a specifically sized and shaped drill bit can be used to create the opening, either in a horizontal or vertical direction through the facet joint.

The bone plug press (graft forming or compression instrument) includes any number of components capable of using harvested autograft, cadaveric allograft cortical bone or a synthetic alternative to match the bone tunnel made by the punch or drill. By way of example only, the bone plug press includes a mechanism similar to common pliers or a more standard hand press that will transfer sufficient force to form bone plugs by squeezing the handles together to form the bone plug and compress the bone or synthetic alternative to the proper density and shape.

The impactor or tamp includes any number of components capable of pushing and compressing the bone plug into the bone tunnels. A suture or metallic overlay also can be applied to provide additional structural stability to the joint during graft incorporation.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION OF THE INVENTION

Figure 1:
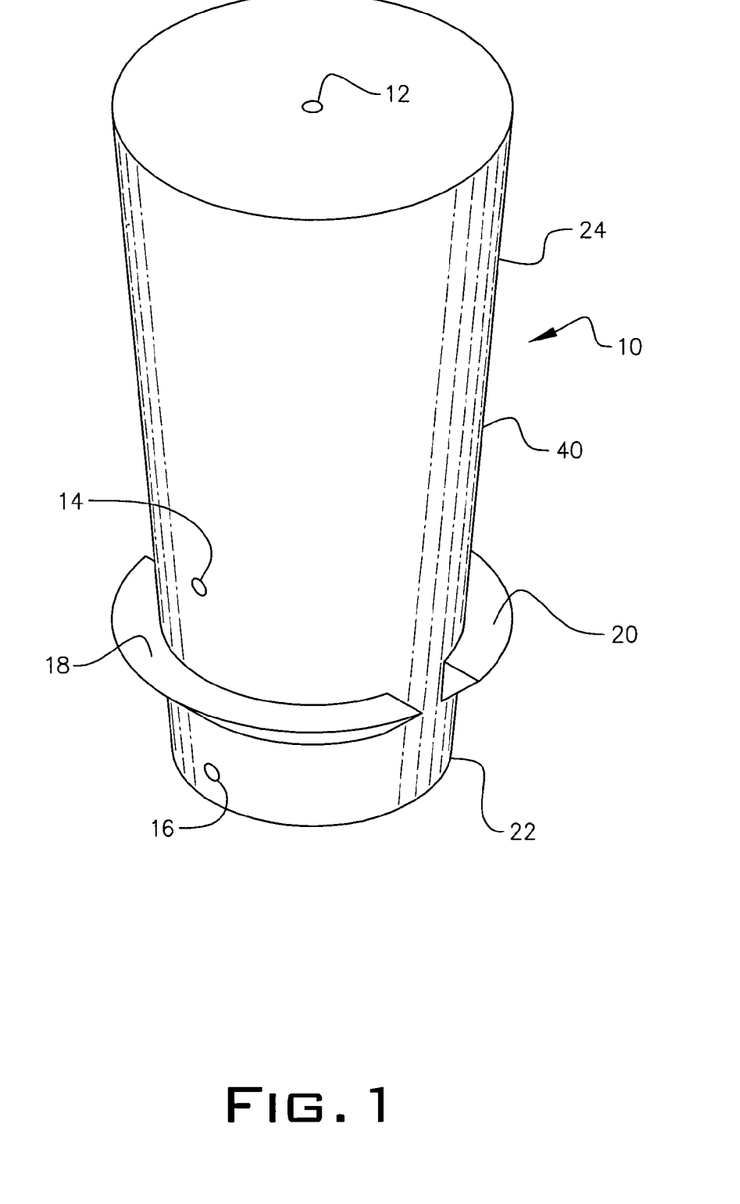
FIG. 1 shows a frustum shaped bone plug of this invention for employment in a facet joint fusion.

Referring to FIG. 1, the bone plug of this invention is an inverted frustum shaped device 10 having a vertical central channel 12 for insertion of a synthetic or biologic material to assist in fusing the bone plug 10 in place in a spinal joint 15. The bone plug 10 has multiple side parts 14 and 16 for excretion of the synthetic or biologic material from the central channel 12. A pair of opposed flanges 18 and 20 on the same plane partially circumvent the bone plug 10 near bottom end 22 having a smaller diameter than the top end 24.

Figure 2:
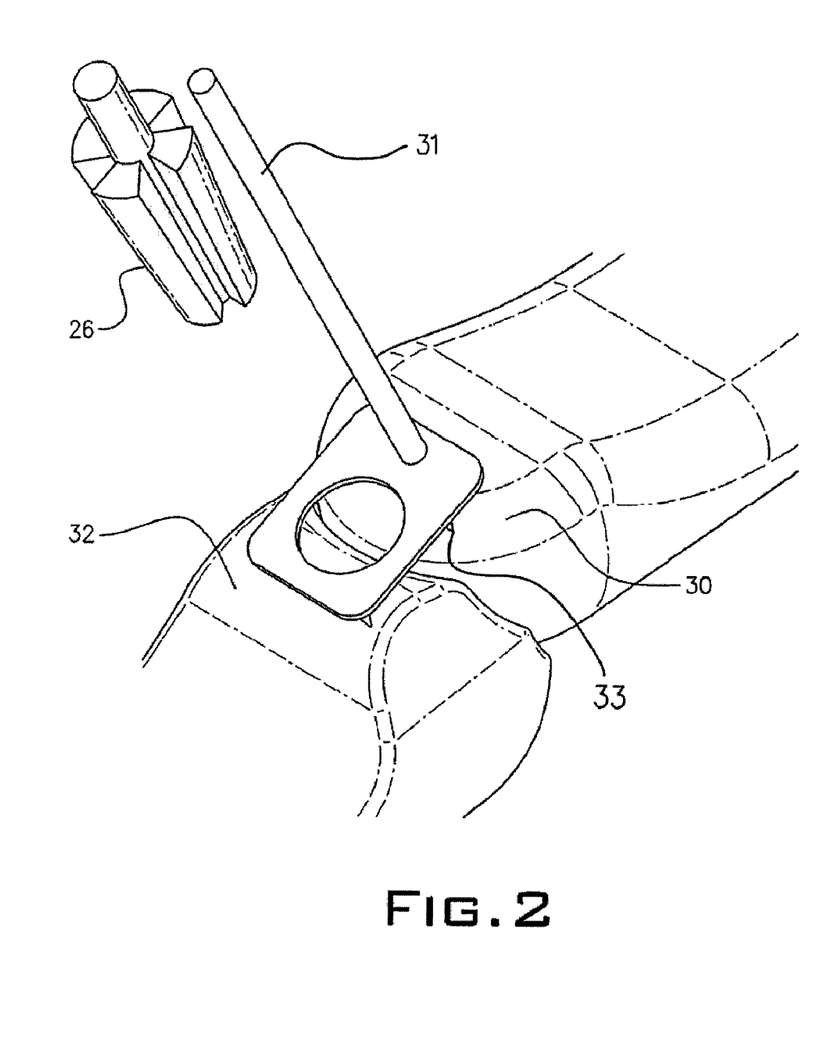
FIG. 2 shows a tapered drill used to prepare for the bone plug.
Figure 3:
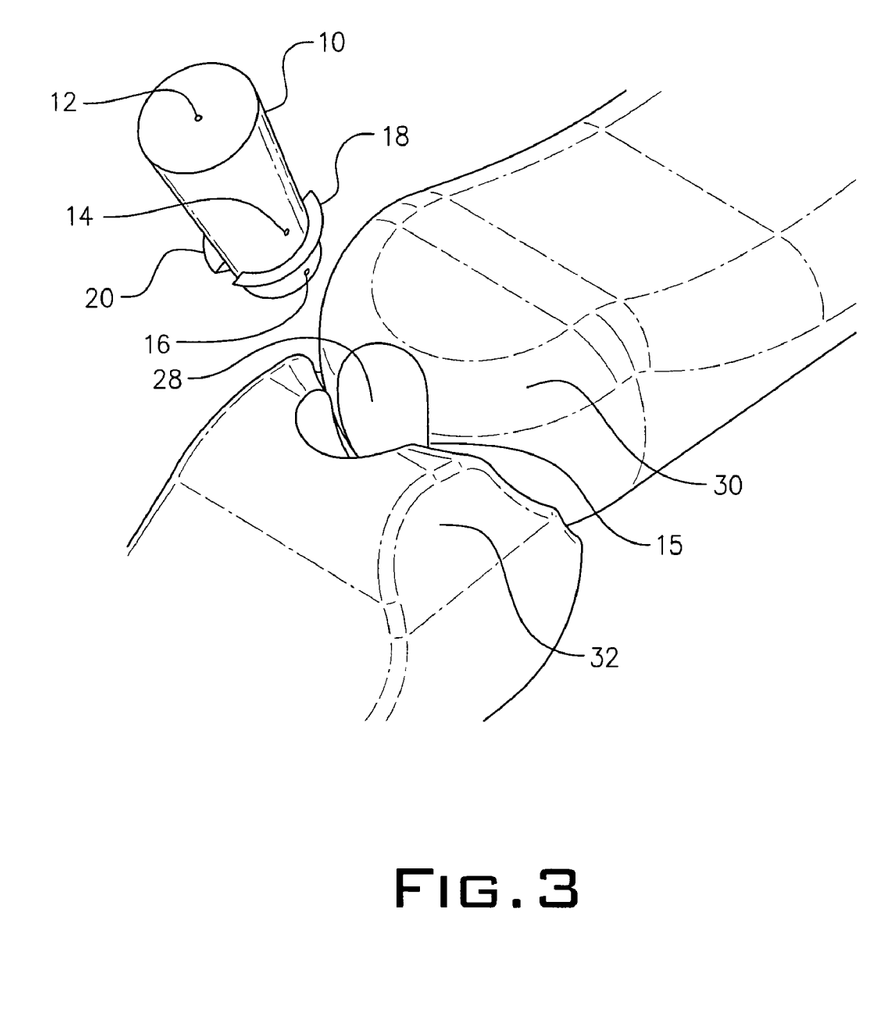
FIG. 3 shows a hole prepared for the bone plug.
Figure 4:
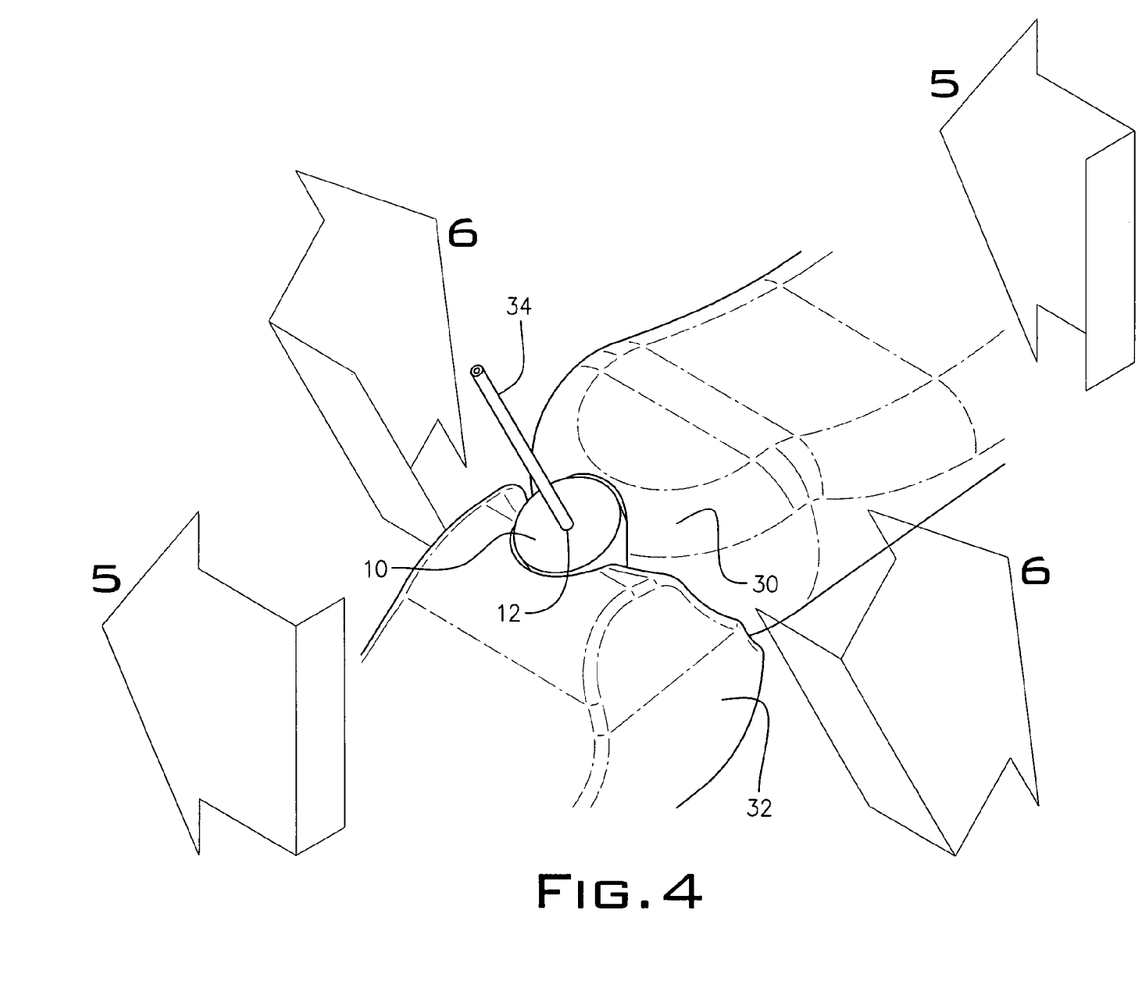
FIG. 4 shows a bone plug inserted in the hole of FIG. 3 and with an application tube for inserting synthetic or biologic material.
Figure 5:
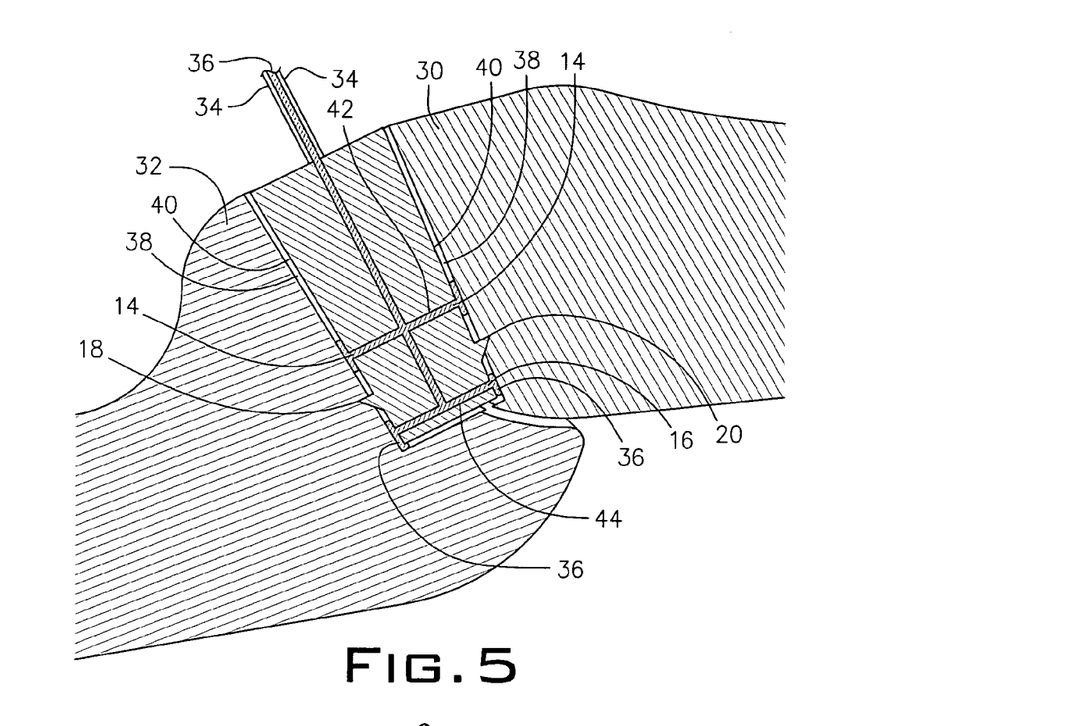
FIG. 5, is a cross-section along line 5-5 of FIG. 4.
Figure 6:
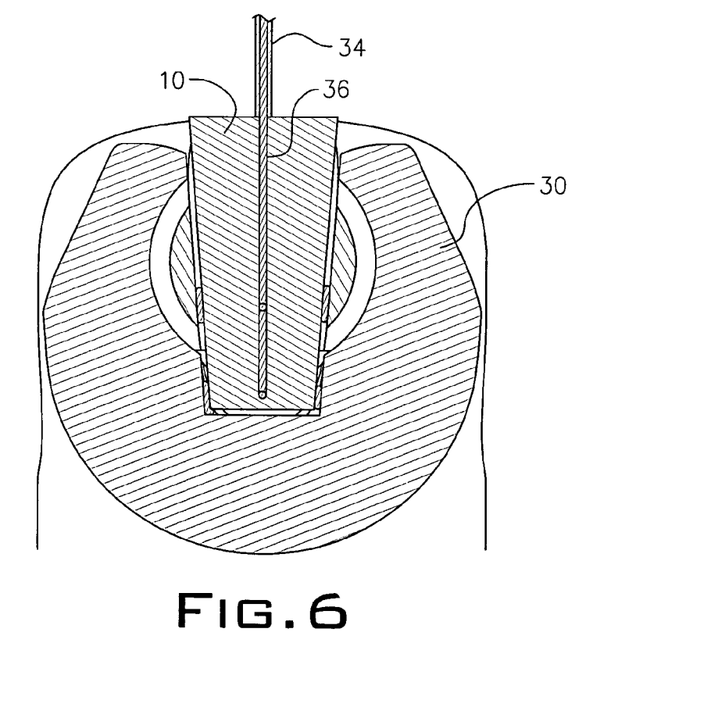
FIG. 6 is a cross-section along ling 6-6 of FIG. 4.
Figure 7:
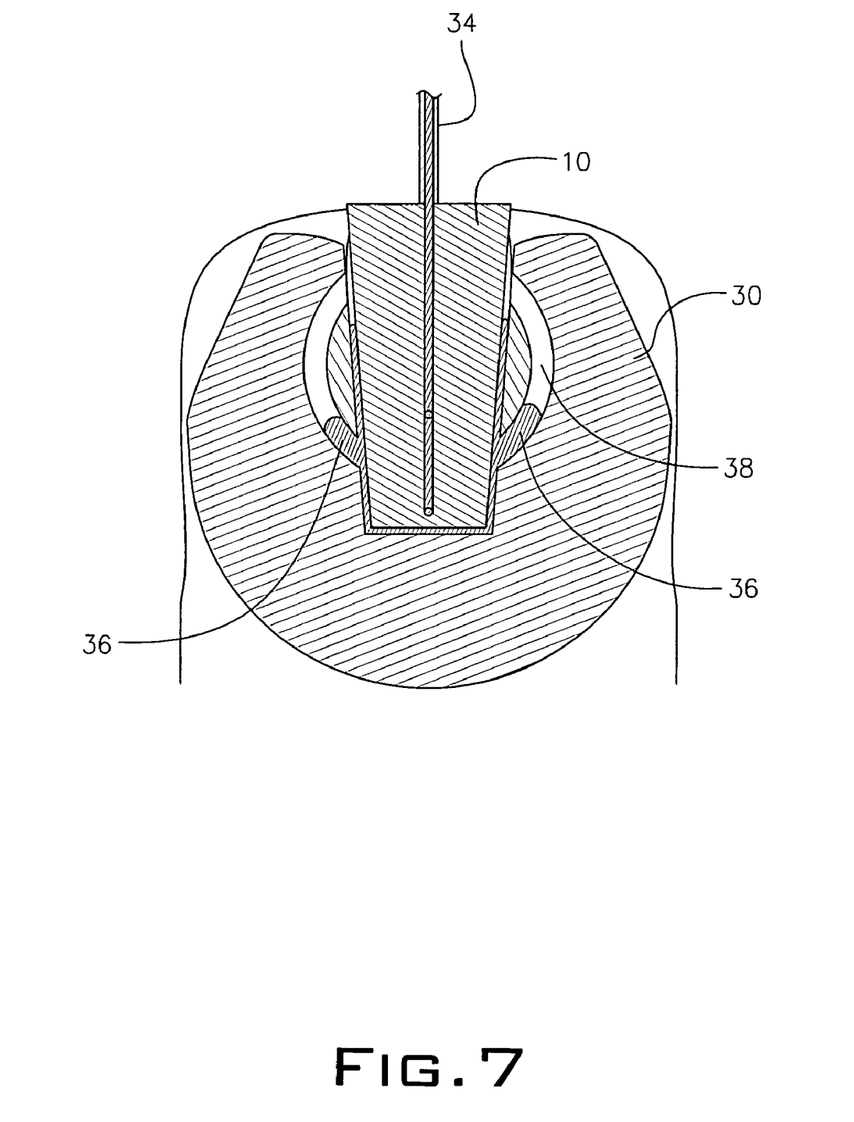
FIG. 7 is a cross-section according to FIG. 6 showing synthetic or biologic material cementing the bone plug in place.

In order to fuse a spinal facet joint, a tapered drill 26, shown in FIG. 2, is employed to prepare a hole 28 shown in FIG. 3 between two bones 30 and 32. A drill guide 31 may be used to guide the tapered drill 26 to prepare the hole 28 in the correct location. Drill guide 31 may be secured to the facet joint by teeth 33 to prevent displacement during hole preparation. As seen in FIG. 4, an application tube 34 is inserted in channel 12 to permit insertion of a synthetic or biologic material 36 into bone plug 10. The biologic material 36 flows down channel 12 as shown in FIG. 5, and excess biologic material flows out of side parts 14 and 16 through channels 42 and 44, respectively, into a space 38 between the bones 30 and 32, and an exterior side wall 40 of the bone plug 10. The flanges 18 and 20 act as detents to hold the bone plug 10 in place within hole 28. As seen further in FIG. 7, the biologic material 36 flows outwardly from openings 14 and 16 into a space 38 to cement the plug 10 in place.

Figure 8:
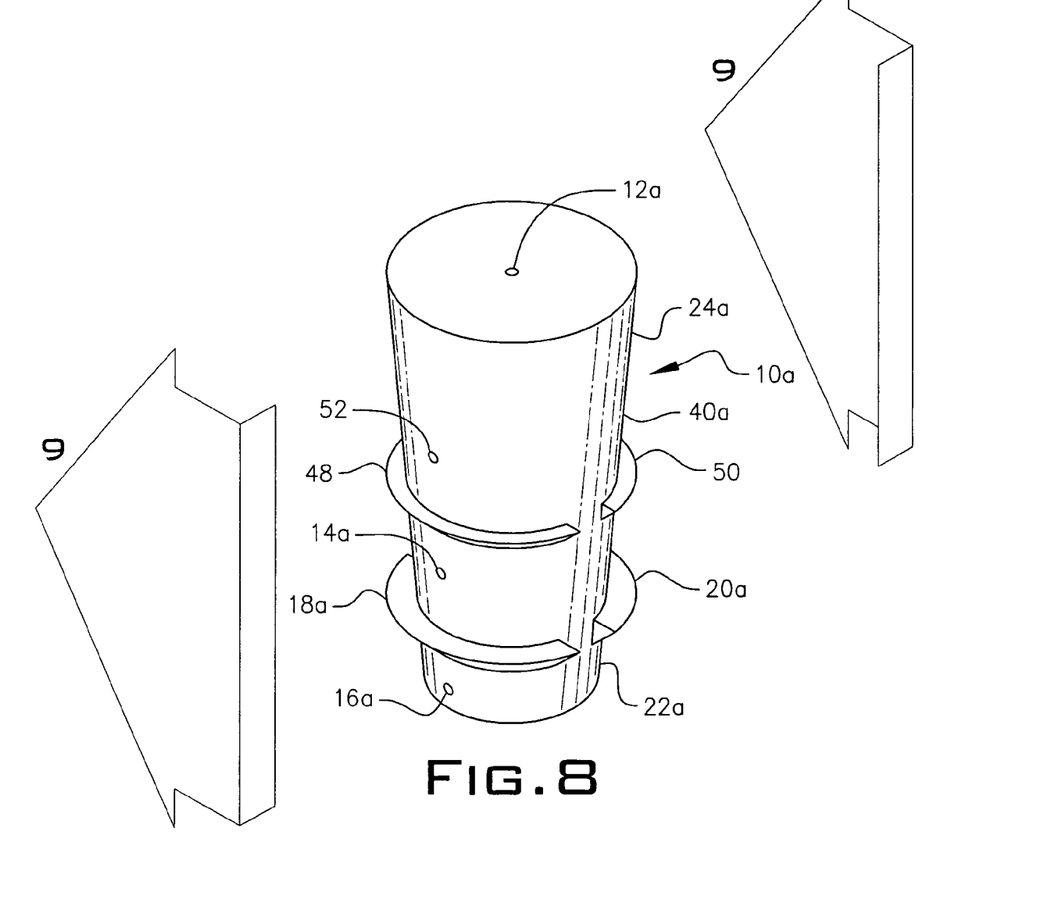
FIG. 8 shows a first alternative frustum shaped bone plug.
Figure 9:
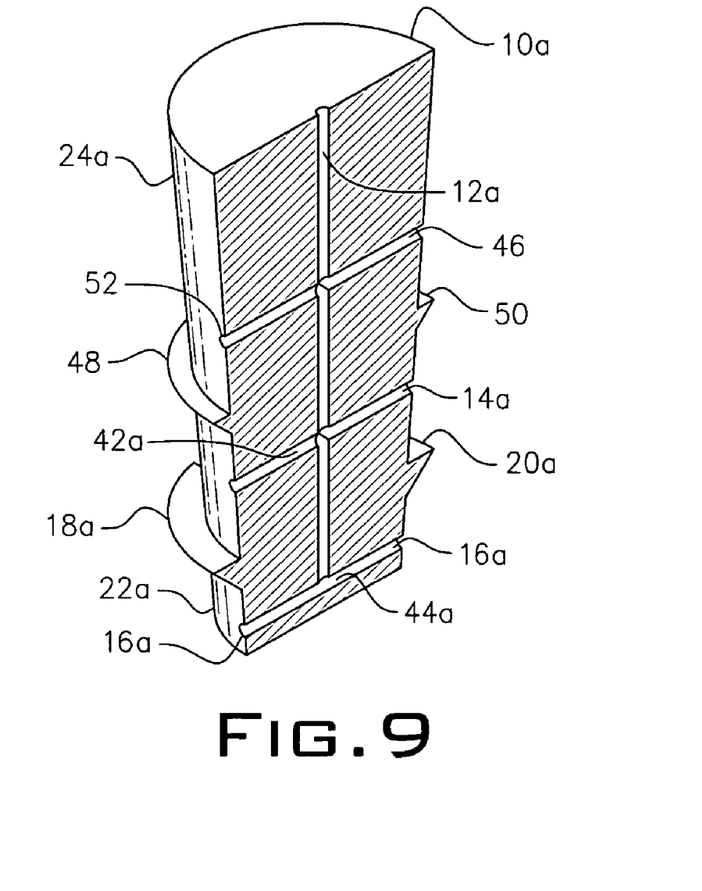
FIG. 9 shows a cross-section of the frustum shaped bone plug of FIG. 8 along lines 9-9.

An alternative plug 10a is shown in FIGS. 8 and 9. A central channel 12a feeds biologic material to side channels 46, 42 and 44a. In like manner, biologic material 36 flows out through openings 52, 14a and 16a and promotes bonding to the bone. A second parallel pair of flanges 48 and 50 are added to flanges 18a and 20a to increase the strength of the plug 10a in the hole 28. Side wall 40a in like manner to plug 10 is narrower in diameter at a bottom end 22a than its top end 24a.

If the joint is determined to be too badly damaged or diseased for present replacement methods or prospective methods such as facet joint hemi-arthroplasty, minimally invasive facet joint fusion is prospectively a superior alternative for three primary reasons:

1. It is minimally invasive surgery that can be performed in an outpatient setting as opposed to major surgery performed in a hospital. This procedure can also be performed during open surgery if the facet joints need to be fused as determined by a physician particularly in conjunction with instrumented vertebral fusion;

2. Recovery times are estimated to be a few weeks as opposed to 6 to 12 months; and 3. It takes full advantage of advances in biomaterials and synthetic alternatives.

The present invention is directed at overcoming, or at least improving upon, the disadvantages of the prior art by achieving the following:

Reversal of the cost/benefit ratio of present procedures versus the invention;

A minimally invasive procedure versus major open surgery;

Outpatient versus inpatient surgery (about 20 minutes per joint versus hours). Note: this procedure may also be performed during open surgery at the discretion of the physician;

Can be used to augment present open fusion techniques to lessen the need for bone stimulation especially in high risk groups such as smokers and multi-level cases;

Reduced morbidity;

Reduced blood loss;

Reduced time under anesthesia;

Reduced risk;

Recovery time dramatically reduced;

Minimal scarring that decreases the risk of failed back syndrome and improves revision surgery outcome;

Reduced risk of post operative infection by significantly reducing operating room time and soft tissue destruction;

No preclusion of other surgical or non-invasive treatment options; and,

Projected high success rate by utilizing accepted arthroscopic procedures employing a new technique and taking advantage of either existing cortical bone harvesting procedures in combination with unique instrumentation to shape and prepare the bone or new pre-shaped, pre-made synthetic cortical bone alternatives as they are made generally available by FDA approval.

It is anticipated that the availability of this system and graft alternatives will dramatically increase the number of surgeries performed because they offer the first safe outpatient surgical solution to the predominant cause of spinal joint pain. It is expected that virtually all patients receiving this procedure will be able to walk out the same day and be fully functional within a few weeks. Present surgical solutions require hospitalization of about three days and six to twenty-four months recovery.

Aside from the obvious positive clinical outcome, the significant favorable financial impact on disability, worker's compensation and health care insurers is considerable.

Spinal facet implant units are calculated per joint. Each patient has two joints per spinal segment and twenty-four segments, C1-C2 through L5-S1 for a total of forty-eight facet joints. Each surgery is likely to involve multiple joints.

The present invention is directed at overcoming, or at least improving upon, the disadvantages of the prior art.

In inserting the plug 10, the tapered drill is specifically used through an arthroscopic type portal allowing access to the joint through a small incision and progressive dilation of the intervening soft tissue. The instrument design does not preclude its use in a classic open surgery or by access to the facet joint through an otherwise limited incision. The opening 28 is marginally smaller than the bone plug 10 to create proper fixation of the plug 10 and the joint.

Figure 10:
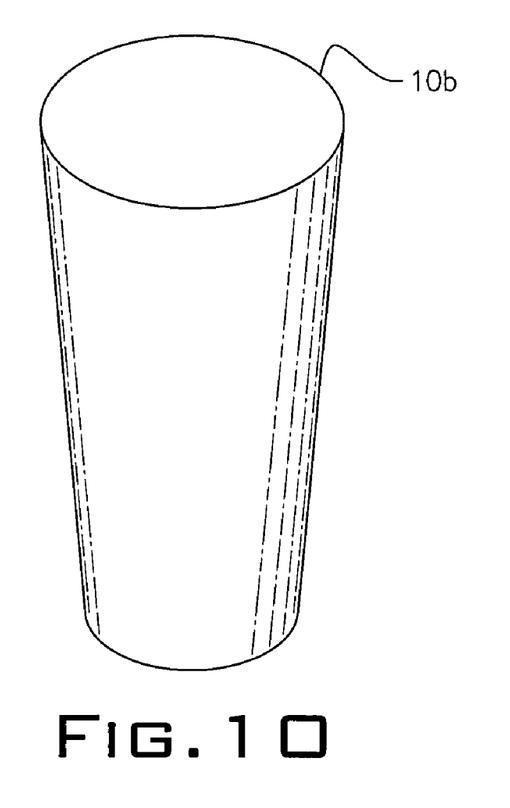
FIG. 10 shows a second alternative frustum shaped bone plug.

Referring again to FIGS. 1 and 8, a fused facet joint plug 10, 10a or 10b is shown with one shaped autograft, cadaveric allograft or FDA approved synthetic pre-made, pre-shaped cortical bone plug. The anterior end 22 or 22a of the plug 10 or 10a is 3-8 mm and the posterior end 24 or 24a of the plug 10, 10a or 10b is 4-12 mm in diameter in a frustum shape with the wider portion located in the posterior portion to facilitate fixation during bone graft incorporation. The procedure is envisioned to require only one bone plug per facet joint and two per level. Permanent fixation occurs when bone in-growth occurs into the joint itself and into the plug over time.

The frustum shaped bone graft 10b, as shown in FIG. 10, can be employed when no additional biologic material is required.

Figure 11:
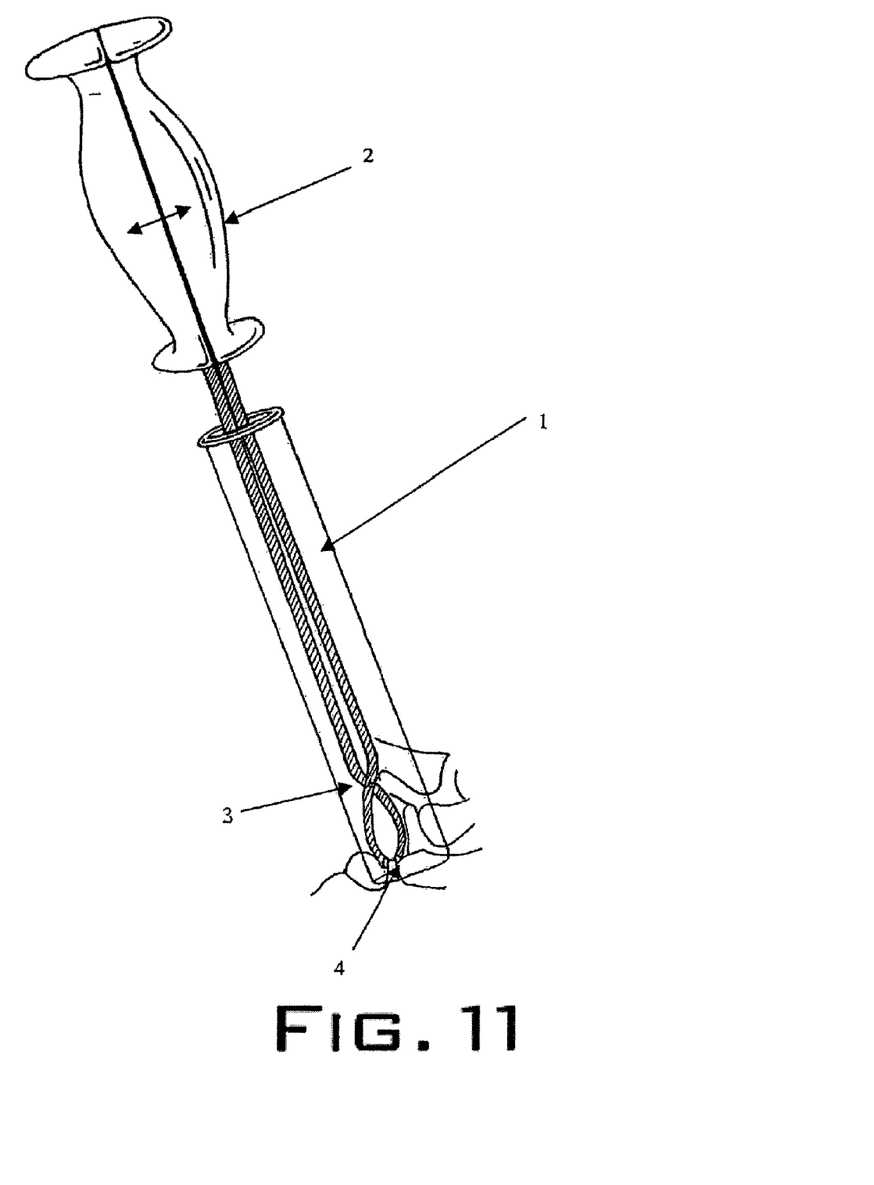
FIG. 11 shows an instrument and arthroscopic portal according to an embodiment of the invention.

FIG. 11 illustrates a bone punch instrument as an embodiment of the invention shown without representation of a press accessory, which can be attached to the punch tips 4 and used to press a bone plug into place. The instrument is specifically invented to be used through an arthroscopic type portal 1 allowing access to the joint through a small incision and progressive dialation of the intervening soft tissue. In this embodiment, arthroscopic type portal 1 comprises a cylindrical tube configured to provide access to a facet joint during surgery. The arthroscopic type portal 1 has an outer surface that prevents the encroachment of surrounding bioligical material into the surgical site at the facet joint and has an inner surface that forms a substantially cylindrical space that provides access to the facet joint for the surgical tools. The instrument design does not preclude its use in a classic open surgery or by access to the facet joint through an otherwise limited incision. A separating handle 2 is specifically designed to provide sufficient mechanical advantage to the punch tips 4. Punch tips of different sizes to create an appropriate opening to receive the sized bone plug selected by a physician. The opening is marginally smaller than the bone plug to create proper fixation of the plug and the joint. Mechanical advangtage created by pressure on the handle is transferred to the punch tips using "X" type joint 3.

Figure 12:
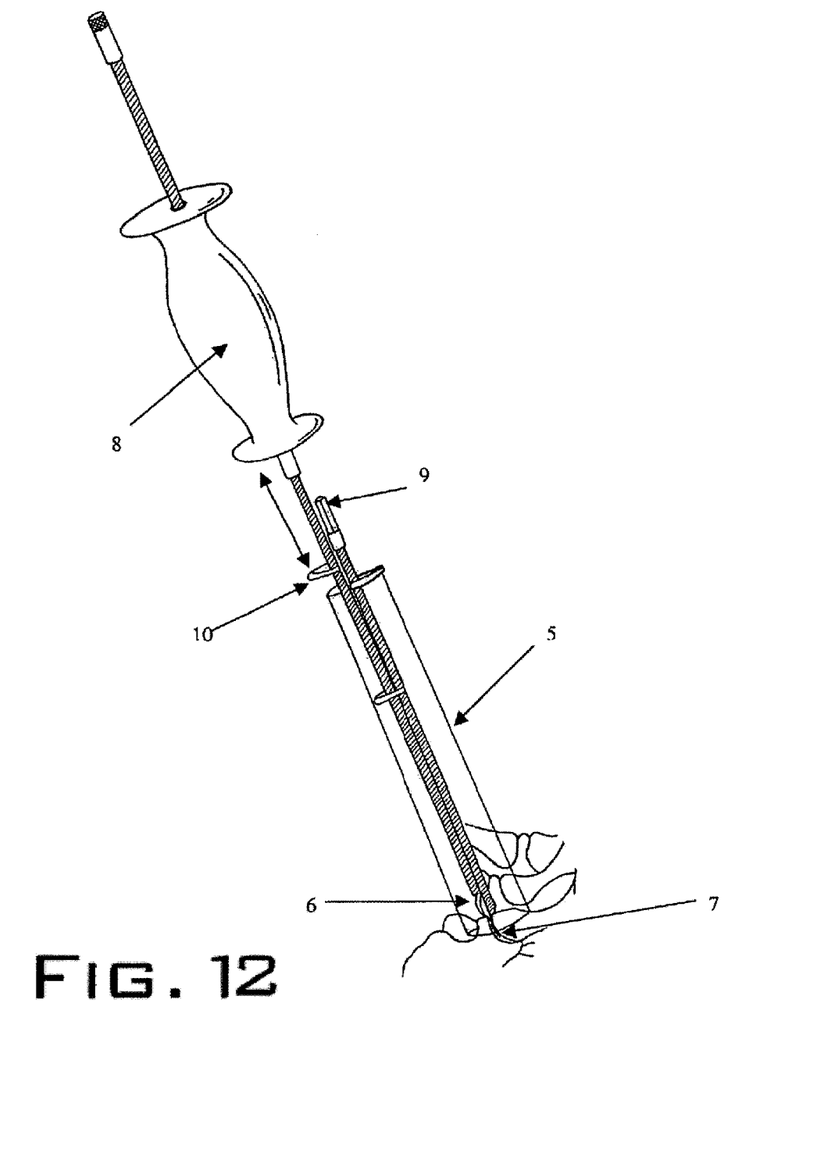
FIG. 12 shows an instrument and arthroscopic portal according to an embodiment of the invention.

FIG. 12 illustrates a specifically designed osteotome as an embodiment of the invention, which accesses the facet joint through an arthroscopic type portal 61 and is used to make a thin slice into the bone on each of the inner surfaces of the joint to prepare the surface to heal together in a permanent fusion. The osteotome is equipped with a specifically sized single use blade 62 shown in situ in the correct aspect into a facet joint 63. The osteotome is impacted with a slap-hammer 65 to make the cuts and is properly positioned using a loop 64 on the osteotome shaft. A protective stop 60 is provided to ensure that the osteotome blade does not penetrate to an unsafe depth.

Other equivalent elements can be substituted for the elements disclosed herein to produce substantially the same results in substantially the same way.

Having thus described the invention what is claimed and desired to be secured by Letters Patent is:

1. An arthroscopic type portal facet surgical method comprising:
    placing a portal into a human patient through a minimally invasive incision in the tissue of said human patient;
    accessing a facet joint through said portal, wherein said facet joint comprises a first facet joint bone and a second facet joint bone, and wherein said first facet joint bone comprises a first articulated surface and said second facet joint bone comprises a second articulated surface, and wherein said first articulated surface and said second articulated surface face each other at said facet joint;
    inserting a drill bit into said portal;
    drilling a hole with said drill bit into said facet joint between said first articulated surface and said second articulated surface through said portal;
    removing said drill bit from said hole through said portal;
    inserting a facet joint fusion plug into said hole through said portal;
    inserting a tamping instrument into said portal; and
    tamping said facet joint fusion plug into said hole with said tamping instrument through said portal.

2. The method of claim 1, wherein said facet joint fusion plug comprises a material selected from one or more of the group consisting of a synthetic bone substitute, a metal bone substitute, a harvested compacted iliac crest graft, an autologous autograft and a cadaveric allograft.

3. The method of claim 1, wherein said hole is a void created by removal of a portion of bone from each of said first articulated surface and said second articulated surface,
    wherein after said removal said remaining portions of said bones define said hole as conically shaped and
    said hole has a shape allowing said facet joint fusion plug to be tamped into said hole.

4. The method of claim 1, wherein said portal comprises an arthroscopic type portal.

5. The method of claim 4, wherein said step of placing said portal into said human patient comprises placing a drill guide into said human patient, wherein said drill guide comprises said arthroscopic type portal.

6. The method of claim 5, wherein said drill guide comprises teeth for maintaining the drill guide proximate to said facet joint.

7. The method of claim 1, wherein said facet joint fusion plug comprises a cadaveric allograft.

8. The method of claim 1, wherein said tamping compresses said facet joint fusion plug in said hole.

9. A method according to claim 1, wherein said facet joint fusion plug comprises a material that can be integrated into said facet joint through bone ingrowth.

10. A method according to claim 1, wherein said facet joint fusion plug comprises a material selected from the group consisting of synthetic cortical bone graft and synthetic non-metallic bone substitute.

11. An arthroscopic type portal facet surgical method comprising:
    placing a portal into a human patient through a minimally invasive incision in the tissue of said human patient;
    accessing a facet joint through said portal, wherein said facet joint comprises a first facet joint bone and a second facet joint bone, and wherein said first facet joint bone comprises a first articulated surface and said second facet joint bone comprises a second articulated surface, and wherein said first articulated surface and said second articulated surface face each other at said facet joint;
    inserting a drill bit into said portal;
    drilling a hole with said drill bit into said facet joint between said first articulated surface and said second articulated surface through said portal;
    removing said drill bit from said hole through said portal;
    inserting a facet joint fusion plug into said hole through said portal; and
    pushing said facet joint fusion plug into said hole through said portal, wherein said facet joint fusion plug comprises bone.

12. The method of claim 11, wherein said hole is a void created by removal of a portion of bone from each of said first articulated surface and said second articulated surface, and
    wherein after said removal said remaining portions of said bones define said hole as conically shaped; and
    said hole has a shape allowing said facet joint fusion plug to be pushed into said hole.

13. The method of claim 11, wherein said bone of said facet joint fusion plug comprises bone from a cadaveric allograft.

14. The method of claim 11, wherein said pushing compresses said facet joint fusion plug in said hole.

15. The method of claim 11, wherein said portal comprises an arthroscopic type portal.

16. The method of claim 15, wherein said step of placing said portal into said human patient comprises placing a drill guide into said human patient, wherein said drill guide comprises said arthroscopic type portal.

17. The method of claim 16, wherein said drill guide comprises teeth for maintaining the drill guide proximate to said facet joint.

18. The method of claim 11, wherein said facet joint fusion plug comprises a material that can be integrated into said facet joint through bone ingrowth.

19. The method of claim 11, wherein said facet joint fusion plug comprises a material selected from the group consisting of synthetic cortical bone graft and synthetic nonmetallic bone substitute.

20. The method of claim 11, wherein said facet joint fusion plug comprises a material selected from one or more of the group consisting of a synthetic bone substitute, a metal bone substitute, a harvested compacted iliac crest graft, an autologous autograft and a cadaveric allograft.

* * * * *

UNITED STATES PATENT AND TRADEMARK OFFICE
CERTIFICATE OF CORRECTION

PATENT NO. : 7,708,761 B2  Page 1 of 2
APPLICATION NO. : 11/232519
DATED : May 4, 2010
INVENTOR(S) : David A. Petersen It is certified that error appears in the above-identified patent and that said Letters Patent is hereby corrected as shown below:

In the drawings:

In FIG. 12, change reference numeral "5" to --61--;

change reference numeral "6" to --62--;

change reference numeral "7" to --63--;

change reference numeral "8" to --65--;

change reference numeral "9" to --64--;

change reference numeral "10" to --60--.

See attached score Fig. 12.

Signed and Sealed this
Twenty-third Day of August, 2011

David J. Kappos
*Director of the United States Patent and Trademark Office*

FIG. 12